(12) United States Patent
Fiehler et al.

(10) Patent No.: US 8,647,364 B2
(45) Date of Patent: *Feb. 11, 2014

(54) TISSUE PUNCTURE CLOSURE DEVICE WITH AUTOMATIC TAMPING

(75) Inventors: William Fiehler, Maple Grove, MN (US); John White, Lakeville, MN (US)

(73) Assignee: St. Jude Medical Puerto Rico LLC, Caguas, PR (US)

(*) Notice: Subject to any disclaimer, the term of this patent is extended or adjusted under 35 U.S.C. 154(b) by 32 days.

This patent is subject to a terminal disclaimer.

(21) Appl. No.: 13/051,786

(22) Filed: Mar. 18, 2011

(65) Prior Publication Data

US 2011/0172702 A1 Jul. 14, 2011

Related U.S. Application Data

(63) Continuation of application No. 10/685,912, filed on Oct. 15, 2003, now Pat. No. 7,931,670.

(51) Int. Cl.
  *A61B 17/08* (2006.01)
  *A61D 1/00* (2006.01)
(52) U.S. Cl.
  USPC ........................................................ 606/213
(58) Field of Classification Search
  USPC ........................................ 606/213–218, 232
  See application file for complete search history.

(56) References Cited

U.S. PATENT DOCUMENTS

| | | | |
|---|---|---|---|
| 4,448,194 A * | 5/1984 | DiGiovanni et al. | 606/145 |
| 5,222,974 A | 6/1993 | Kensey et al. | |
| 5,411,520 A | 5/1995 | Nash et al. | |
| 5,441,517 A | 8/1995 | Kensey et al. | |
| 5,531,759 A | 7/1996 | Kensey et al. | |
| 5,545,178 A | 8/1996 | Kensey et al. | |
| 5,662,681 A | 9/1997 | Nash et al. | |
| 5,779,719 A | 7/1998 | Klein et al. | |
| 5,861,004 A | 1/1999 | Kensey et al. | |
| 6,007,563 A | 12/1999 | Nash et al. | |
| 6,045,569 A | 4/2000 | Kensey et al. | |
| 6,086,607 A | 7/2000 | Cragg et al. | |
| 6,090,130 A | 7/2000 | Nash et al. | |
| 6,860,895 B1 | 3/2005 | Akerfeldt et al. | |
| 2006/0229672 A1 | 10/2006 | Forsberg | |
| 2006/0229673 A1 | 10/2006 | Forsberg | |
| 2006/0229674 A1 | 10/2006 | Forsberg | |
| 2006/0265006 A1 | 11/2006 | White et al. | |
| 2006/0265007 A1 | 11/2006 | White et al. | |

* cited by examiner

*Primary Examiner* — Melanie Tyson
(74) *Attorney, Agent, or Firm* — Holland & Hart

(57) ABSTRACT

A method and apparatus for sealing a puncture or incision formed percutaneously in tissue separating two internal portions of the body of a living being with an anchor, a sealing plug and a filament connecting the anchor and sealing plug. The method and apparatus provide for automatic tamping and/or cinching of the sealing plug when the apparatus is withdrawn from the puncture site. The automatic tamping and/or cinching is facilitated by transducing a motive force generated by the withdrawal of the apparatus into a tamping and/or cinching force.

20 Claims, 9 Drawing Sheets

# TISSUE PUNCTURE CLOSURE DEVICE WITH AUTOMATIC TAMPING

RELATED APPLICATION

This is a continuation of U.S. patent application Ser. No. 10/685,912, filed on 15 Oct. 2003, now issued as U.S. Pat. No. 7,931,670, the disclosure of which is incorporated, in its entirety, by this reference.

FIELD OF THE INVENTION

This invention relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., a catheter) can pass through the sheath and to an operative position within the vascular system. Intravascular and intraluminal procedures unavoidably present the problem of stopping the bleeding at the percutaneous puncture after the procedure has been completed and after the instrument (and any insertion sheaths used therewith) has been removed. Bleeding from puncture sites, particularly in the case of femoral arterial punctures, is typically stopped by utilizing vascular closure devices, such as those described in U.S. Pat. Nos. 6,179,863; 6,090,130; and 6,045,569, which are hereby incorporated by this reference.

Typical closure devices such as the ones described in the above-mentioned patents place a sealing plug at the tissue puncture site. Successful deployment of the sealing plug, however, requires that it be manually ejected from within a device sheath and tamped down to an outer surface of the tissue puncture using a tamping tube. The tamping procedure cannot commence until the device sheath (within which the tamping tube is located) has been removed so as to expose the tamping tube for manual grasping. Under certain conditions, removal of the sheath prior to tamping the sealing plug may cause the sealing plug itself to be retracted from the tissue puncture, hindering subsequent placement of the sealing plug, and resulting in only a partial seal and associated bleeding from the tissue puncture. Accordingly, there is a need for improving the mechanism for deployment of the sealing plug at the site of a tissue puncture

SUMMARY

In one of many possible embodiments, the present invention provides a tissue puncture closure device for partial insertion into and sealing of an internal tissue wall puncture. The closure device includes a filament extending from a first end of the closure device to a second end of the closure device, an anchor for insertion through the tissue wall puncture attached to the filament at the second end of the closure device, a sealing plug slidingly attached to the filament adjacent to the anchor, and an automatic driving mechanism for automatically tamping or cinching the sealing plug toward the second end upon withdrawal of the closure device from the internal tissue wall puncture. The device may include a tamping tube disposed adjacent to the sealing plug, such that the tamping tube is driven by the automatic driving mechanism to tamp the sealing plug.

According to some embodiments the automatic driving mechanism includes a transducer for effecting a tamping force on the sealing plug upon withdrawal of the closure device from the tissue wall puncture. The transducer may include mechanical, electrical, and/or optical components.

According to one embodiment the transducer includes a spool with a portion of the filament wound thereon, a gear engaged with the spool, and a tamping tube driver directly or indirectly driven by the gear. The tamping tube driver may be a flexible rack or a rigid tube slidingly disposed about the filament. The spool rotates and drives the gear, and the gear drives the tamping tube driver when the anchor is deployed and the closure device is retracted from the tissue wall puncture. The gear may in fact be a gear train with a gear ratio of at least 2.5:1 with respect to the spool. A torque-limiting clutch may be disposed between the spool and the gear according to some embodiments, and according to some embodiments the tamping tube driver may also act as the tamping tube.

According to some embodiments of the present invention, the transducer includes an electronic switch at the proximal end of the closure device and a motor operatively connected to the electronic switch. Retraction of the closure device from the tissue wall puncture trips the electronic switch and activates the motor to generate the tamping force on the seal plug. The motor may include, for example, a servo or solenoid that actuates a linear tamping force on the seal plug.

According to some embodiments, the transducer includes an optical sensor operatively connected to a motor for detecting or measuring withdrawal of the closure device from the tissue wall puncture and generating a signal upon withdrawal of the closure device from the tissue wall puncture. The signal generated by the optical sensor may be transduced to an electrical signal activating the motor and generating the tamping force on the seal plug.

According to one embodiment there is a tissue puncture closure device for partial insertion into and sealing of a tissue puncture in an internal tissue wall accessible through a percutaneous incision including an anchor for disposition on a distal side of the internal tissue wall, a sealing plug for disposition on a proximal side of the internal tissue wall, a filament connected to and anchored at a distal end to the anchor and sealing plug for slidably cinching the anchor and sealing plug together about the tissue puncture, wherein the sealing plug is slidably disposed on the filament proximal to the anchor, a tamping tube disposed on the filament for driving the sealing plug along the filament distally towards the anchor, a storage spool onto which a proximal end of the filament is wound; a first gear engaged with the storage spool, where withdrawal of the closure device from the tissue puncture retracts the filament from the storage spool and actuates the first gear to directly or indirectly provide a tamping force to the tamping tube.

According to another aspect of the invention there is a method of sealing a tissue puncture in an internal tissue wall accessible through a percutaneous incision including withdrawing a closure device from the tissue puncture, and automatically transducing a motive force generated by withdrawal of the closure device in a first direction to a cinching or tamping force in a second direction. The method may further include applying the tamping force in the second direction to a sealing plug. The method may also include transferring the motive force to a rack that is slidingly disposed about a filament connected to the sealing plug. The transferring may include automatically unwinding the filament from a spool by deploying an anchor attached to the filament inside the tissue puncture, and withdrawing the closure device from the tissue puncture. The spool rotation may thus act as the motive force. The transferring may also include driving a gear train operatively connected to tamping tube with the spool.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Figure 1:
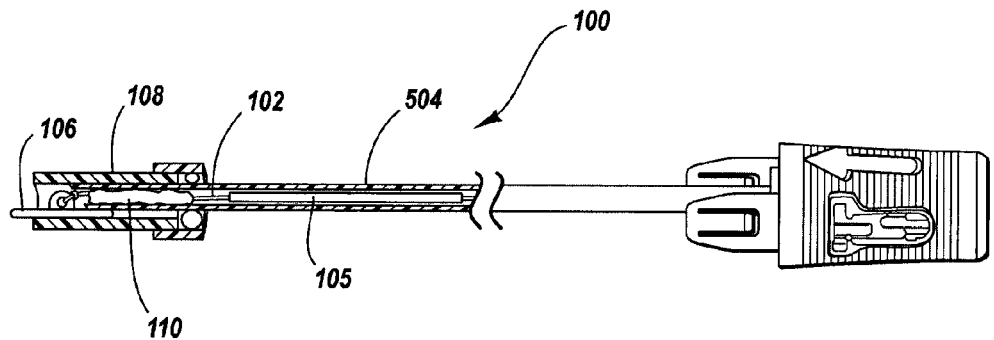
FIG. 1 is a cut-away view of a tissue closure device according to the prior art.
Figure 2:
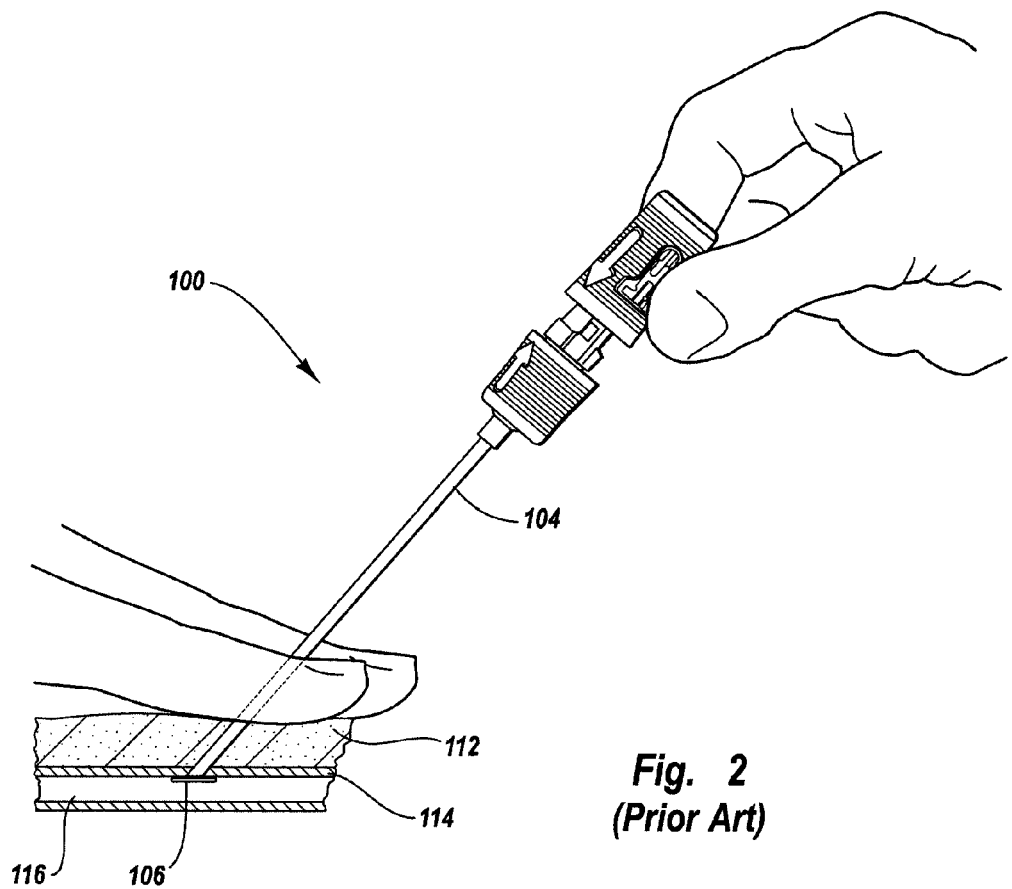
FIG. 2 is a side view of the tissue closure device of FIG. 1 engaged with an artery according to the prior art.

Turning now to the figures, and in particular to FIGS. 1-4, a typical tissue puncture closure device 100 is shown. Referring to FIG. 1, the typical tissue puncture closure device 100 includes a suture 102 pre-threaded down through an elongated carrier tube 104 and a tamping tube 105. The suture 102 extends through a collagen sponge 110, then through an anchor 106 located exterior to a distal end 108 of the carrier tube 104 and back into the carrier tube 104, where it is again attached to the collagen sponge 110 disposed on the suture 102 and within the carrier tube 104. As shown in FIG. 2, the sheath 104 is normally inserted through an incision in a patient's skin 112 and through a puncture in a tissue wall 114 until the anchor 106 is deployed within a luminal cavity 116 of an organ or artery. The collagen sponge 110 (FIG. 1) remains outside of the luminal cavity 114.

Figure 3:
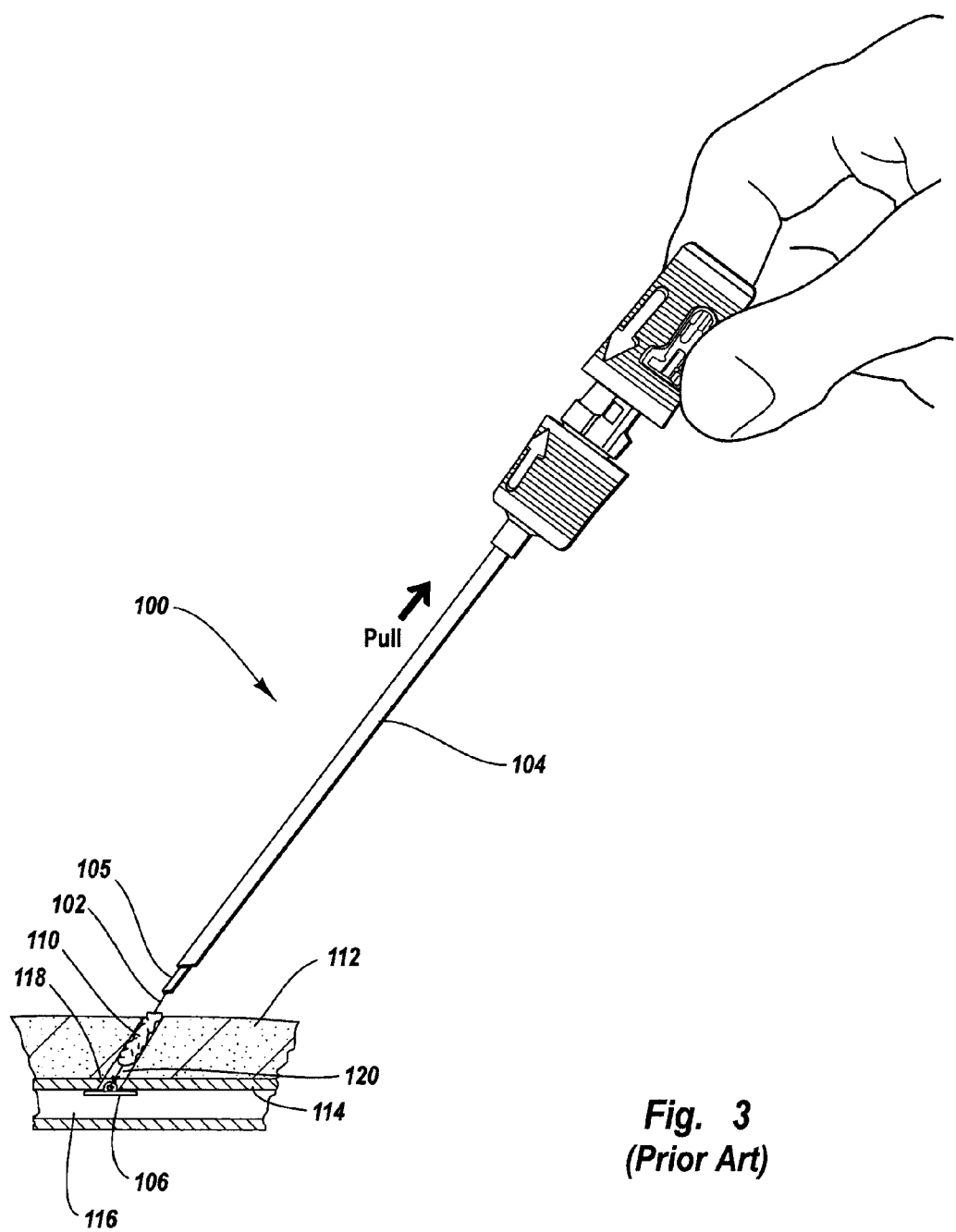
FIG. 3 is a side view of the tissue closure device of FIG. 1 being withdrawn from an artery according to the prior art to deploy a collagen sponge.
Figure 4:
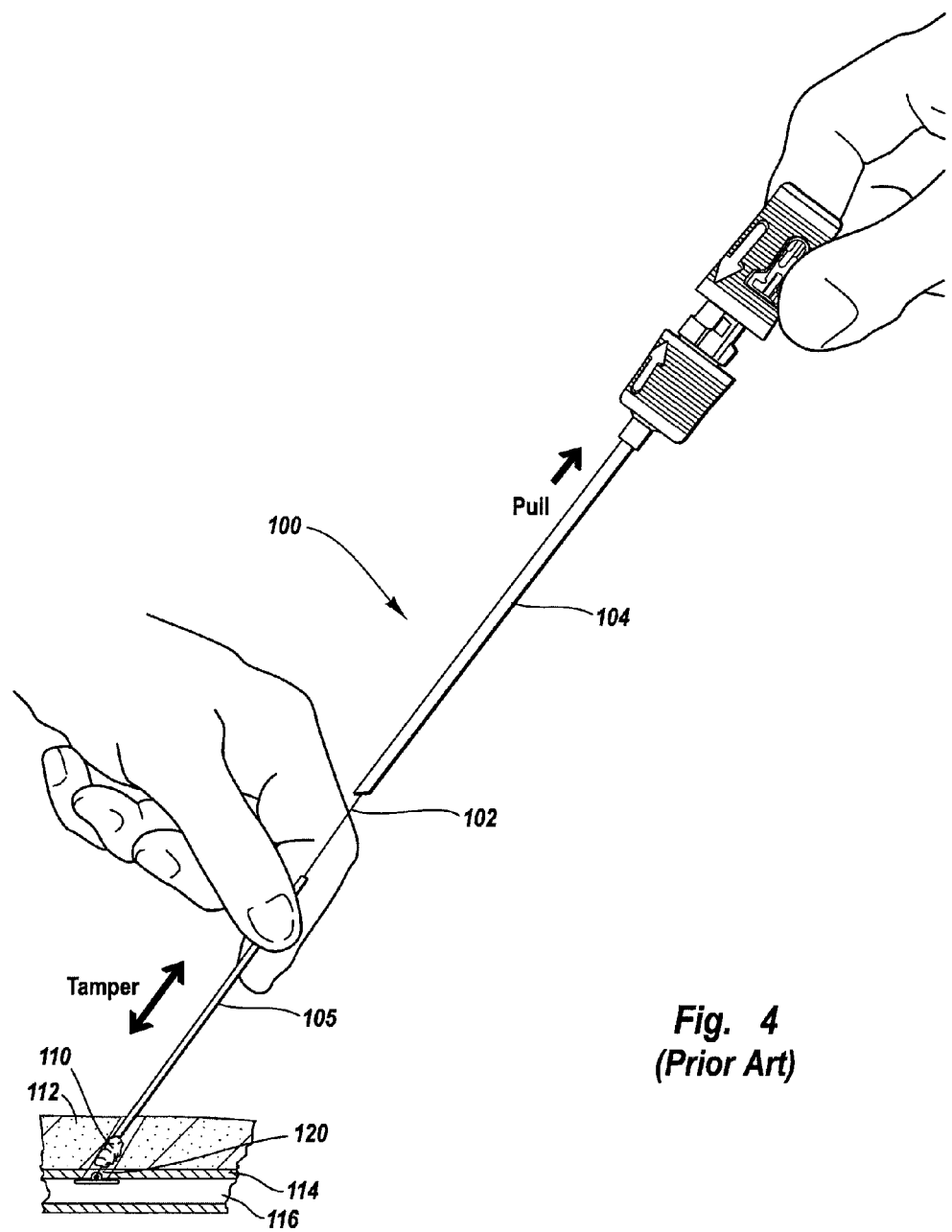
FIG. 4 is a side view of the tissue closure device of FIG. 1 illustrating tamping of the collagen sponge according to the prior art.

Referring next to FIGS. 3-4 and as mentioned above, successful deployment of the collagen sponge 110 to plug the puncture typically requires that the sponge be manually exposed from within the sheath 104 and tamped down to an outer surface 118 of the tissue puncture using the tamping tube 105, while simultaneously pulling on the suture 102 to cinch tight the suture 102 connecting the anchor 106 and collagen sponge 110. Accordingly, the sheath 104 is withdrawn from the puncture as shown in FIGS. 3-4 to expose the collagen sponge 110 and the tamping tube 105. As the suture 102 is pulled and the collagen sponge 110 is tamped with the tamping tube 105, the anchor 106 and the collagen sponge 110 are brought together and held in place with a self-tightening slip-knot on the suture 102. Thus, the tissue puncture is sandwiched between the anchor 106 and collagen sponge 110, thereby sealing the tissue puncture. The suture 102 is then cut and the incision may be closed. The suture 102, anchor 106, and collagen sponge 110 are generally made of resorbable materials and therefore may remain in place while the puncture heals.

Using the typical tissue puncture closure device 100 described above, however, the tamping of the collagen sponge 110 cannot commence until the sheath 104 has been removed so as to expose the tamping tube 105 for manual grasping. Under certain conditions, removal of the sheath 104 prior to tamping the collagen sponge 110 causes the collagen sponge 110 itself to be retracted from the tissue puncture, creating a gap 120 between the collagen sponge 110 and the puncture. The gap 120 may remain even after tamping as shown in FIG. 4, and sometimes results in only a partial seal and bleeding from the tissue puncture.

Therefore, the present specification describes a tissue puncture closure device that automatically drives a sealing plug toward a tissue puncture upon withdrawal of the tissue puncture closure device from the tissue puncture site. While the preferred embodiments of the tissue puncture closure device are shown and described below, the principles of the present specification may be incorporated into any of a number of tissue closure devices. The specific embodiments described below are for illustrative purposes only, and are not limiting.

As described above, the general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Figure 5:
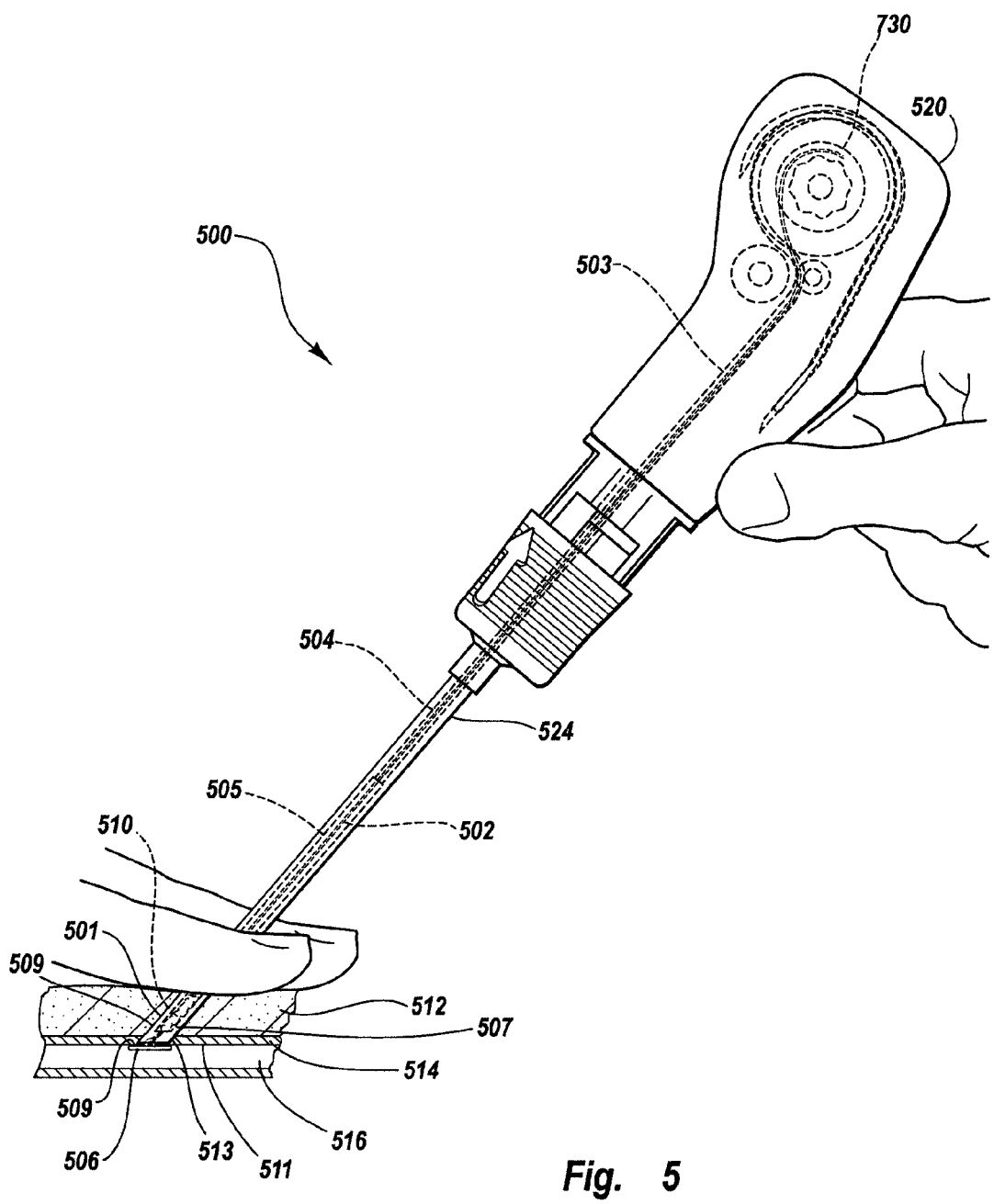
FIG. 5 is a side view of a tissue closure device with an automatic tamper mechanism shown engaged with an artery according to one embodiment of the present invention.

As used in this specification and the appended claims, the term "tamp" or "tamping" is used broadly to mean packing down by one or a succession of blows or taps. Further, the term "effecting" means producing an outcome, achieving a result, or bringing about. Referring now to FIG. 5, a tissue closure device 500 according to one embodiment of the present invention is shown. The closure device 500 has particular utility when used in connection with intravascular procedures, such as angiographic dye injection, cardiac catheterization, balloon angioplasty and other types of recanalizing of atherosclerotic arteries, etc. as the closure device 500 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and can be used for sealing punctures or incisions in other types of tissue walls as well. Thus, the sealing of a percutaneous puncture in an artery, shown herein, is merely illustrative of one particular use of the tissue closure device 500 of the present invention.

The tissue closure device 500 includes a first or proximal end 503 and a second or distal end 507. A carrier tube 504 extends from the proximal end 503 to the distal end 507 and includes an outlet 513. The carrier tube 504 may be made of plastic or other material and is designed for insertion through a sheath (104) which is designed for insertion through a percutaneous incision 501 in a tissue layer 512 and into a lumen 516. According to FIG. 5, the lumen 516 defines an interior portion of a femoral artery 514.

The distal end 507 of the carrier tube 504 also includes an anchor 506 and a sealing plug 510. The anchor 506 of the present embodiment is an elongated, stiff, low-profile member arranged to be seated inside the artery 514 against an artery wall 511 contiguous with a puncture 513. The anchor 506 is preferably made of a biologically resorbable polymer. The sealing plug 510 is formed of a compressible sponge or foam, also made of a non-hemostatic biologically resorbable material such as collagen, and may be configured in any shape so as to seal the tissue puncture 513.

The sealing plug 510 and anchor 506 are connected to one another by a suture or filament 502 that is also biologically resorbable. The anchor 506, sealing plug 510, and suture 502 are collectively referred to as the "closure elements" below. As shown in FIG. 5, the anchor 506 is arranged adjacent to and exterior of the distal end 507 of the sheath 524, while the sealing plug 510 is initially disposed within carrier tube 504. While the anchor 506 is shown deployed with a first surface 509 against the artery wall 511, it will be understood that initially the anchor is arranged axially along the carrier tube 504 to facilitate insertion into the lumen 516 (see, for example the anchor 106 of FIG. 1).

The suture 502 extends distally from the first end 503 of the closure device 500 through the carrier tube 504. The suture 502 is threaded through perforations in the sealing plug, then through a hole in the anchor 506 and proximally back through the carrier tube 504 to the sealing plug 510. The suture 502 is preferably threaded through a perforation or series of perforations in the sealing plug 510. The suture 502 may also be threaded around itself to form a slip-knot. The suture 502 thus connects the anchor 506 and the sealing plug 510 in a pulley-like arrangement that serves to cinch the anchor 506 and the sealing plug 510 together when the carrier tube 504 is pulled away from the anchor 506 and the sealing plug 510, sandwiching and locking the anchor and plug together and thereby sealing the tissue puncture 513.

The carrier tube 504 also includes a tamping device, such as a tamping tube 505, for tamping the sealing plug 510 along the suture 502 and against the anchor 506. The tamping tube 505 is shown located within the carrier tube 504 and proximal of the sealing plug 506. The tamping tube 505 is an elongated tubular member that may be rigid or flexible and formed of any suitable material. For example, according to one embodiment the tamping tube 505 is made of polyethylene. The suture 502 extends through the tamping tube 505 but is not directly connected thereto. Accordingly, the suture 502 and tamping tube 505 are free to slide past one another. According to the embodiment of FIG. 5, as the suture 502 extends beyond a proximal end of the tamping tube 505 and attaches to an automatic driving mechanism 730 located within a housing 520 at the first end 503 of the closure device 500. Embodiments of the automatic driving mechanism are described in detail below with reference to FIGS. 7 and 8.

In practice, the carrier tube 504 of the closure device 500 (containing the closure elements described above) is inserted into an insertion sheath 524, which is already inserted within the artery 514. As the closure device 500 and the associated closure elements are inserted into the insertion sheath 524, the anchor 506 passes through and out of a distal end 509 of the insertion sheath 524 and is inserted into the artery lumen 516.

As mentioned above, the anchor 506 is initially arranged substantially parallel with the carrier tube 504 to facilitate insertion of the anchor 506 through the percutaneous incision 501 and into the lumen 516.

The closure device 500 is then withdrawn from the insertion sheath 524 until the anchor 506 catches on the distal end 509 of the insertion sheath 524 and rotates to the position shown in FIG. 5. When resistance to further retraction of the closure device 500 is felt by an operator, the closure device 500 and the insertion sheath 524 are withdrawn together, causing the anchor 506 to anchor itself within the artery 514 against the artery wall 511. With the anchor 506 anchored within the artery 514 at the puncture site 513, further retraction of the closure device 500 and insertion sheath 524 causes the sealing plug 510 to withdraw from the distal end 507 of the carrier tube 504, thereby depositing the plug within the incision or puncture tract 501.

Figure 6:
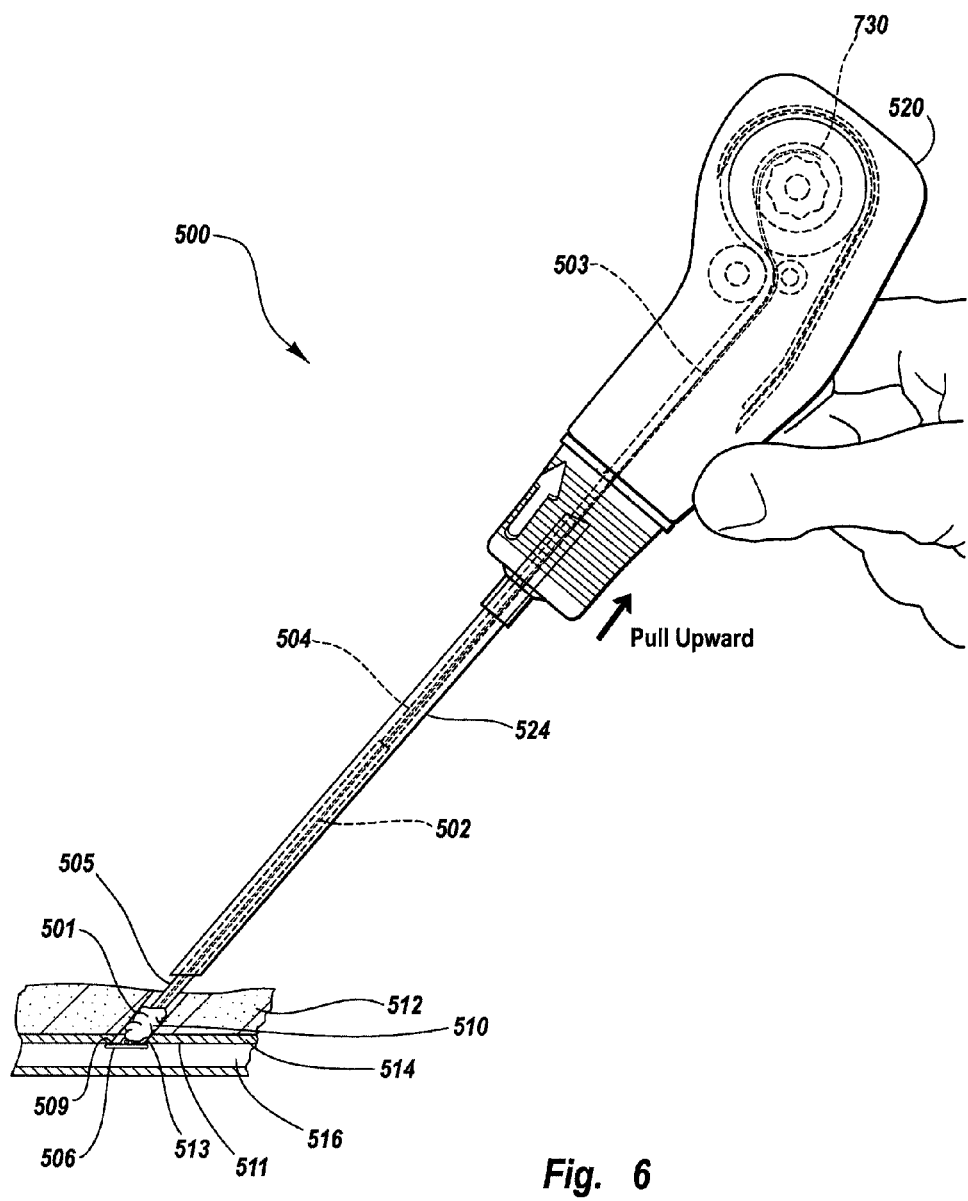
FIG. 6 is a side view of the tissue closure device of FIG. 5 being withdrawn from an artery according to one embodiment of the present invention.

However, unlike previous closure devices that require a separate, manual tamping procedure following the deposition of the sealing plug 510, the closure device 500 of the present invention automatically tamps the sealing plug 510. The closure device 500 drives the tamping tube 505 toward the sealing plug 510 automatically upon withdrawal of the closure device 500 from the puncture tract, tamping the plug toward the anchor 506 as shown in FIG. 6. Therefore, the sealing plug 510 is tamped while the carrier tube 504 is still arranged adjacent to the puncture 513 in the femoral artery 514, reducing or eliminating any gaps that may otherwise occur between the sealing plug 510 and the puncture 513 in the femoral artery 514.

In addition, by placing tension on or pulling the suture 502 away from the puncture tract, the suture 502 cinches and locks (with a slip knot or the like) together the anchor 506 and the sealing plug 510, sandwiching the artery wall 511 between the anchor 506 and sealing plug 510. The force exerted by the tamping tube 505 and the cinching together of the anchor 506 and sealing plug 510 by the filament 502 also causes the sealing plug 510 to deform radially outward within the puncture tract and function as an anchor on the proximal side of the tissue puncture site 513.

Figure 7:
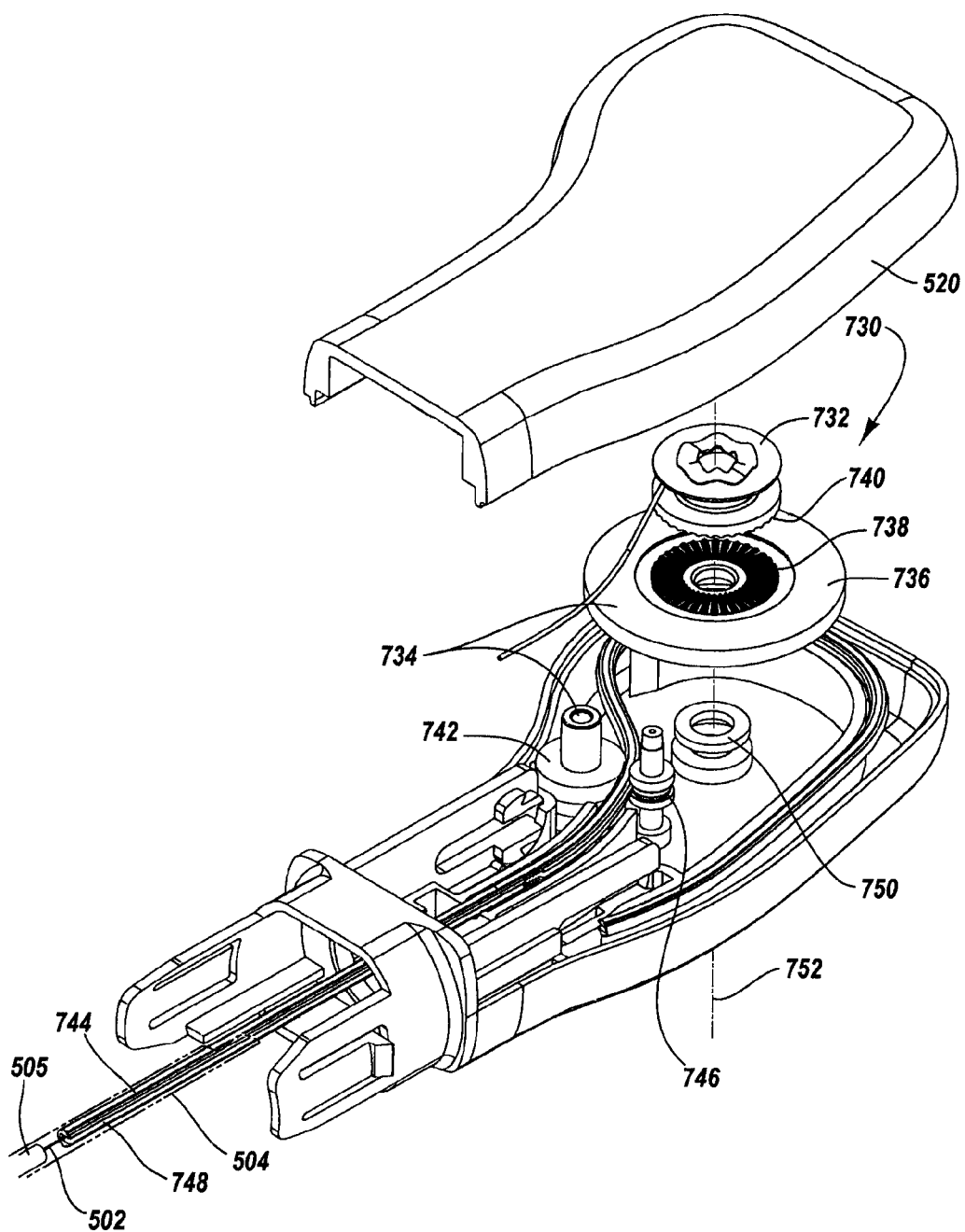
FIG. 7 is an assembly view of a tissue closure device with an automatic tamping mechanism according to one embodiment of the present invention.

Automatically driving the tamping tube 505 toward the sealing plug 510 and/or cinching the plug and the anchor 506 may be facilitated by any of a number of mechanisms. For example, one automatic driving mechanism 730 that may be disposed in the housing 520 of the closure device 500 is shown in FIG. 7. According to the embodiment of FIG. 7, retraction of the closure device 500 automatically effects tamping of the sealing plug 506 (FIG. 6). The automatic transducement of the retraction to tamping is achieved, according to FIG. 7, by the automatic driving mechanism 730.

According to the automatic driving mechanism 730 of FIG. 7, the suture 502 is connected to and wound about a spool 732. Withdrawal of the closure device 500 (FIG. 6) from the tissue puncture site (if the anchor 506 (FIG. 6) is deployed) causes the suture 502 to unwind from the spool 732. The spool 732 rotates as the suture 502 unwinds and provides a torsional motive force that may be transduced to a linear tamping force.

Transducing the torsional motive force provided by the spool 732 to the tamping force is achieved by a gear train 734 according to the embodiment of FIG. 7. The gear train 734 includes a first gear 736 arranged coaxially with the spool 732. The first gear 736 and the spool 732 may include mating fan surfaces 738, 740, respectively. The mating fan surfaces 738, 740 define a torque-limiting clutch that prevents the transmission of exceptional torsional forces from the spool 732 to the first gear 736 that exceed a predetermined level.

The matching fan surfaces 738, 740 of the first gear 736 and storage spool 732 may be forced into engagement by a biasing member, such as a compressible washer 750, with sufficient force to cause mechanical or frictional engagement of the fan gears surfaces 738, 740, while still permitting mutual rotation about an axis of rotation 752. The fan surfaces 738, 740 are preferably sinusoidally shaped so as to permit slippage between the fan surfaces 738, 740 only when torsional forces reach or exceed a predetermined level. It will be understood, however, that other fan surface shapes may also be used, including, but not limited to, V-shapes, square shapes and flat surfaces. The predetermined torsional force level necessary to overcome the mechanical or frictional engagement of the fan surfaces 738, 740 may be modified by adjusting the frequency or amplitude of the sinusoidally shaped fan faces, by adjusting the biasing force between the fan surfaces 738, 740, or by any other convenient method.

As shown in FIG. 7, the first gear 736 may engage a second gear 742. The first and second gears 736 and 742 may engage one another with a frictional fit or with gear teeth (not shown). The second gear 742 also engages and drives a tamping tube driver, for example a flexible rack 744 that is disposed between the second gear 742 and roller guide 746. The flexible rack 744 may be referred to as a tamping member. At least a portion of the flexible rack 744 at least partially wraps around at least one of the first and second gears 736, 742. When the spool 732 rotates, the flexible rack 744 drives the tamping tube 505, which in turn drives the sealing plug 510 (FIG. 6). Alternatively, the flexible rack 744 may act as a tamping tube itself and therefore become the "tamping tube 505."

The flexible rack 744 is preferably a semi-tubular member that is disposed about the suture 502 along its longitudinal axis and within the carrier tube 504 and housing 520 of the closure device 500. The semi-tubular shape of the rack 744 has a generally U-shaped cross section, and provides a channel or shaft 748 through which the suture 502 extends. The open channel 748 permits the suture and the rack 744 to merge as the spool 732 winds or unwinds. The suture 502 and the flexible rack 744 are not fixedly connected to one another, allowing each to slide freely past the other.

It may be desirable in some cases to increase the linear velocity of the flexible rack 744 relative to the linear velocity at which the closure device 500 (FIG. 6) may be withdrawn. An increased linear velocity for the flexible rack 744 may better assure that the sealing plug 510 (FIG. 6) is forced toward the anchor 506 (FIG. 6) while the closure device 500 (FIG. 5) is being withdrawn in an opposite direction. Therefore, according to some embodiments, the gear train 734 may have an overall gear ratio greater than 1:1. For example, the gear ratio may range between approximately 2.5:1 and 6.0:1 for some embodiments, while gear ratio is about 5.0:1 in other embodiments.

However, it should be noted that the linear velocity of the flexible rack (or other tamping driver) should not be excessively greater than the linear velocity of withdrawal of the closure device, as excessive speed could potentially force the sealing plug 510 through the tissue puncture and into the lumen 516 of the artery 514. Likewise, an insufficient opposing force against the anchor 506 could potentially result in the anchor being pulled out of place from within the artery. Therefore, according to some uses the withdrawal force should not exceed approximately 2.5 pounds. It will be understood by those of skill in the art having the benefit of this disclosure that the drive spool/gear train configuration shown in FIG. 7 is exemplary in nature, and not limiting. Any gear configuration (including the configuration described below with reference to FIG. 8) may be used to transmit a motive force generated by retraction of the suture 502 from the closure device 500 (FIG. 6) to provide an automatic driving force to the sealing plug 510 (FIG. 6). In addition, the torque-limiting clutch may be arranged at any point along the gear train 734 and is not limited to the engagement between the spool 732 and the first gear 736.

Operation of the embodiment of FIG. 7 is as follows. As the closing device 500 (FIG. 6) is retracted from a puncture tract, the suture 502, which is threaded through the anchor 506 (FIG. 6), unwinds from and causes rotation of the spool 732. The spool 732 drives the first gear 736 as it rotates via the mating engagement between the fan surfaces 738, 740. As the first gear 736 rotates it drives the second gear 742, and the second gear 742 drives the flexible rack 744. The flexible rack 744 drives the tamping tube 505, which tamps the sealing plug 510 (FIG. 6). Therefore, as the closing device 500 (FIG. 6) is retracted from the puncture tract, the sealing plug 510 (FIG. 6) is automatically tamped via the automatic driving mechanism 730. Accordingly, the seal plug 510 (FIG. 6) is more likely to create a sufficient arterial seal without gaps between the seal plug 510 (FIG. 6) and the anchor 506 (FIG. 6), as may otherwise occur with a separate manual tamping procedure.

Figure 8:
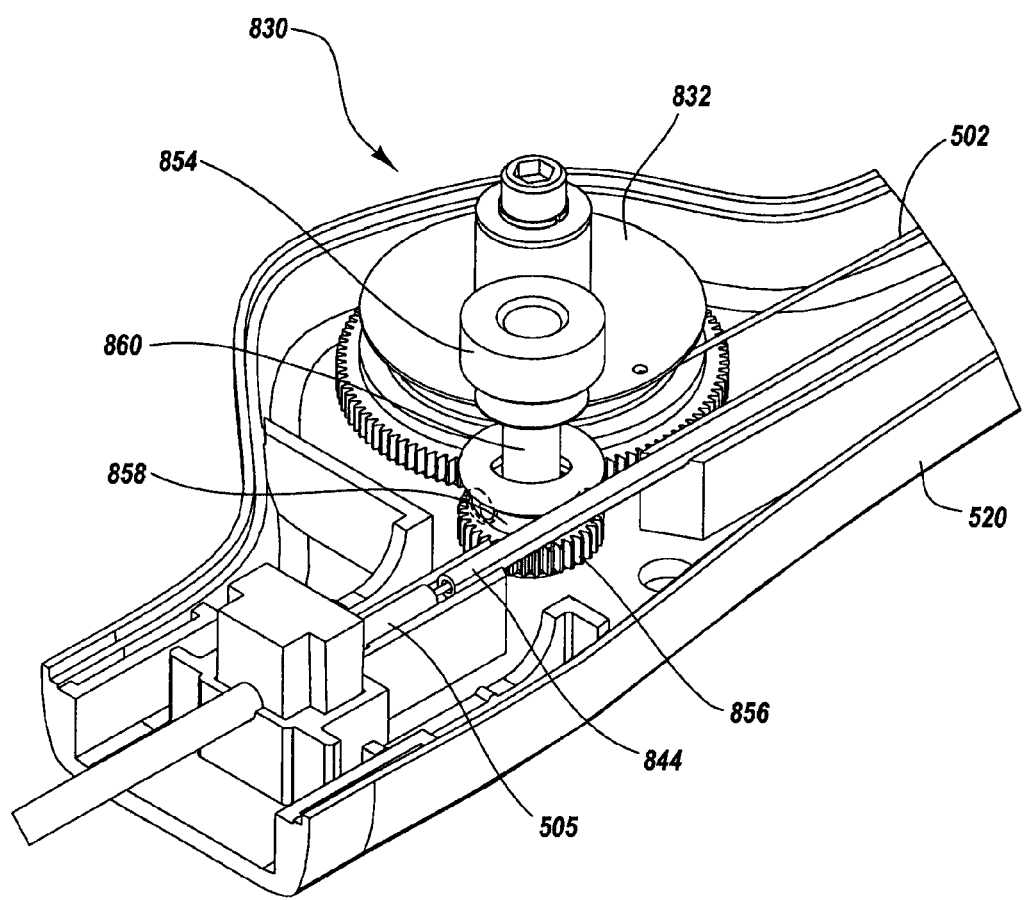
FIG. 8 is a cut away view of a tissue closure device with an automatic tamping mechanism according to another embodiment of the present invention.

Referring next to FIG. 8, another embodiment of an automatic driving mechanism 830 is shown. According to the embodiment of FIG. 8, the automatic driving mechanism 830 includes a combination spool/drive gear 832. The suture 502 is connected to and wound about the spool/drive gear 832. Similar to the operation of the driving mechanism of FIG. 7, withdrawal of the closure device 500 (FIG. 6) from the tissue puncture site causes the suture 502 to unwind from the spool/drive gear 832. The spool/drive gear 832 rotates as the suture 502 unwinds, and provides a motive force that is transduced to a linear tamping force.

Transducement of the motive force from the spool/drive gear 832 is achieved as the spool/drive gear 832 engages a drive wheel 854. The drive wheel 854 includes a pinion gear 856 that directly engages pinions of the spool/drive gear 832 according to the embodiment of FIG. 8. Similar to the arrangement between the spool 732 and the first gear 736 of FIG. 7, the drive wheel 854 of FIG. 8 is designed to limit transmission torque by slipping with respect to a mounting hub 860 if the tangential force transmitted by the spool/drive gear 832 reaches or exceeds a predetermined level. The drive wheel 854 also includes a surface or recess 858 that provides a frictional engagement with a rigid or flexible tamping tube driver 844.

The tamping tube driver 844 may drive the tamping tube 505, which in turn drives the sealing plug 510 (FIG. 6) when the spool/drive gear 832 rotates. Alternatively, the tamping tube driver 844 may extend a sufficient length to act as a tamping tube itself and therefore become the "tamping tube 505." The tamping tube driver 844 includes a shaft through which the suture 502 freely extends. The free sliding movement between the tamping tube driver 844 and the suture 502 allows the suture 502 to unwind in one direction while the tamping tube driver 844 moves in an opposite direction to tamp the sealing plug 510 (FIG. 6).

As mentioned with reference to FIG. 7, it may be desirable in some cases to increase the linear velocity of the tamping tube driver 844 relative to the linear velocity at which the closure device 500 (FIG. 6) may be withdrawn. Therefore, according to some embodiments, a gear ratio between the spool/driver gear 832 and the pinion gear 856 may be greater than 1:1. For example, the gear ratio may range between approximately 2.5:1 and 6.0:1 for some embodiments, while gear ratio is about 5.0:1 in other embodiments.

Figure 9A:
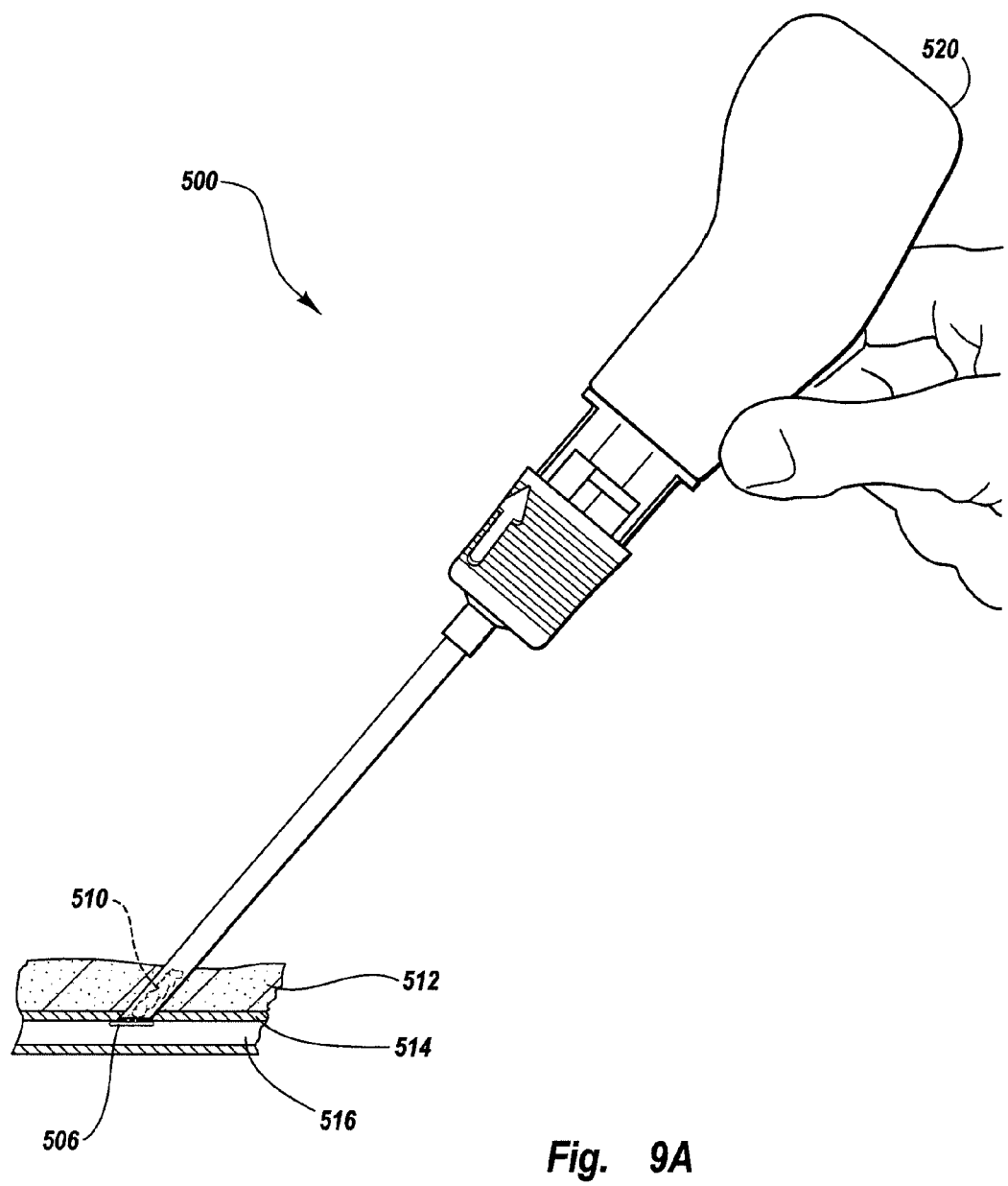
FIG. 9A is a side view of a tissue closure device with an electrical or optical automatic tamping mechanism according to one embodiment of the present invention.
Figure 9B:
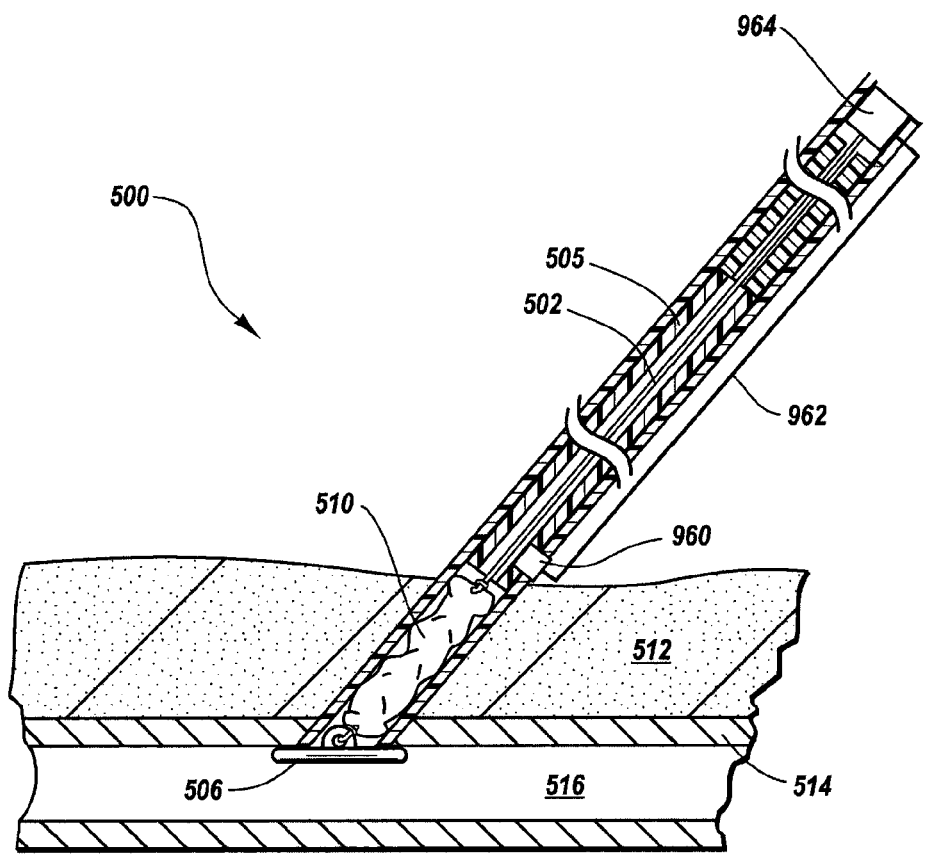
FIG. 9B is a cross-sectional detail of the tissue closure device of FIG. 9A.

Although two of the embodiments shown and described above (FIGS. 7-8) illustrate mechanical transducers that may be used to convert forces associated with retraction of the closure tool 500 to an automatic tamping force on the sealing plug 510, other transducers may also be used according to principles of the invention to facilitate automatic tamping of the sealing plug 510. Any means for transducing a motive force in a first direction to a subsequent force in another direction may be used. For example, referring to FIGS. 9A-B, electrical switches and/or optical transducers may be used to generate an automatic tamping force upon retraction of the closure tool 500 from a puncture tract. Accordingly, an electrical switch and/or optical sensor 960 may transmit a signal along a communications interface 962 to a motor, servo, solenoid, or other device 964 indicating retraction of the closure device 500. The motor, servo, solenoid, or other device 964 may then provide a tamping force when the signal is received.

Therefore, according to some embodiments the proximal end of the suture 502 may be operatively connected to the electronic switch 960 that is operatively connected to the motor 964 (and/or a power source). Retraction of the suture 502 from the closure device 500 may trip the electronic switch 960 and activate the motor 964 to generate a force used to tamp the sealing plug 510. Similarly, the electronic switch 960 may be or include an optical sensor for detecting and/or measuring withdrawal of the closure device 500 from the tissue puncture and generating a signal indicating withdrawal of the closure device from the tissue puncture. The optical signal may be transduced to an electrical signal, and the electrical signal may be transmitted to the motor 964 (and/or a power source) for generating a driving or tamping force to the sealing plug 510. The motor, servo, solenoid, or other device 964 may be rotary for generating torsional force (which may be transduced to linear motive force in a manner similar to that described above), or linear for generating a force that may be directly or indirectly applied to the sealing plug 510.

The tissue closure device 500 described above may be particularly useful following an intravascular procedure, such as angioplasty or catheterization. Therefore, the general steps that may be taken for such a procedure are described below, followed by a number of steps that may be taken according to some methods prior to use of the tissue closure device 500.

According to a standard intravascular procedure, a cannula of an instrument, such as an angiographic needle, is inserted through the skin into an artery, such as the femoral artery, at the situs for the instrument's insertion. The needle cannula is held in place and a flexible guidewire is then passed through the cannula longitudinally into the artery until it reaches a desired depth. Once the guidewire is in place, the needle cannula is removed, leaving the guidewire in place. A procedure sheath and an arterial dilator are then passed over the guidewire, through the puncture or incision, and into the artery. The guidewire and then the dilator are removed, leaving the procedure sheath in place. A catheter or other intravascular instrument is then inserted through the procedure sheath and through the artery to the desired intravascular location, e.g., the situs of an atherosclerotic occlusion. Upon completion of the intravascular procedure (e.g., angioplasty), the catheter is removed, leaving the procedure sheath in place.

The procedure sheath may then be used to facilitate introduction of the closure device 500. First, another guidewire is used to assist in locating the artery. The procedure sheath may then be removed, leaving the guidewire in place. The insertion sheath 524 with an arterial dilator is then inserted along the guidewire, through the percutaneous incision and tissue puncture, and into the artery. The guidewire and dilator are removed, and the insertion sheath 524 left in place is then used for accessing the tissue puncture with the tissue closure device 500 as described above.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
   a filament;
   an anchor attached to the filament;
   a sealing plug slidingly attached to the filament and positioned adjacent to the anchor;
   a tamping member disposed adjacent to the sealing plug;
   an automatic driving mechanism including at least one gear and being configured to compact the sealing plug with the tamping member upon withdrawal of the closure device, a portion of the tamping member being engaged by the at least one gear, and rotation of the at least one gear advances the tamping member.

2. A tissue puncture closure device according to claim 1 wherein the automatic driving mechanism comprises a transducer comprising:
   a storage spool with a portion of the filament wound thereon;
   the at least one gear engaged with the storage spool.

3. A tissue puncture closure device according to claim 2 wherein the storage spool rotates and drives the at least one gear, and the at least one gear drives the tamping member when the anchor is deployed and the closure device is retracted from a tissue puncture.

4. A tissue puncture closure device according to claim 2 further comprising a torque limiting clutch disposed between the storage spool and the at least one gear.

5. A tissue puncture closure device according to claim 2 wherein the tamping member is directly driven by the at least one gear.

6. A tissue puncture closure device according to claim 1 wherein the tamping member comprises a flexible tube or a rigid tube slidingly disposed about the filament.

7. A tissue puncture closure device for partial insertion into and sealing of a tissue puncture in an internal tissue wall accessible through a percutaneous incision, comprising:
   an anchor configured to be disposed on a distal side of the internal tissue wall;
   a sealing plug configured to be disposed on a proximal side of the internal tissue wall;
   a filament connected to the anchor and sealing plug and configured to slidably cinch the anchor and sealing plug together about the tissue puncture;
   a tamping tube disposed on the filament and configured to drive the sealing plug along the filament distally toward the anchor;
   a storage spool onto which a portion of the filament is wound;
   a first gear driven by rotation of the storage spool;
   a second gear;
   wherein at least a portion of the tamping tube engages the at least one of the first and second gears, and withdrawal of the tissue puncture closure device relative to the tissue puncture provides compaction of the sealing plug with the tamping tube.

8. A tissue puncture closure device according to claim 7, wherein withdrawal of the closure device from the tissue puncture while the anchor remains disposed on the distal side of the internal tissue wall unwinds the filament from the storage spool and actuates the first gear to directly provide a tamping force to the tamping tube.

9. A tissue puncture closure device according to claim 7, wherein the tamping member comprises a flexible tube or a rigid tube.

10. A tissue puncture closure device according to claim 7, further comprising a torque limiting clutch disposed between the spool and the first gear.

11. A tissue puncture closure device according to claim 7 wherein the spool and the first gear are arranged coaxially.

12. A tissue puncture closure device, comprising:
   a sealing plug;
   a tamping member;
   an automatic driving mechanism including at least one gear and being configured to compact the sealing plug with the tamping member upon withdrawal of the closure device, a portion of the tamping member being engaged by the at least one gear, and rotation of the at least one gear advances the tamping member.

13. The tissue puncture closure device according to claim 12 further comprising a filament, the sealing plug being slidingly attached to the filament.

14. A tissue puncture closure device according to claim 13 wherein the automatic driving mechanism comprises a transducer comprising:
   a storage spool with a portion of the filament wound thereon;
   the at least one gear engaged with the storage spool.

15. A tissue puncture closure device according to claim 14 wherein the tamping member comprises a flexible rack or a rigid tube slidingly disposed about the filament.

16. A tissue puncture closure device according to claim 12 wherein the automatic driving mechanism comprises a storage spool with a portion of the filament wound thereon, wherein the storage spool rotates and drives the at least one gear, and the at least one gear drives the tamping member.

17. A tissue puncture closure device according to claim 16 further comprising a torque limiting clutch disposed between the storage spool and the at least one gear.

18. A tissue puncture closure device according to claim 16 wherein the at least one gear includes a first gear engaged with the tamping member, and a second gear arranged coaxial with and driven by rotation of the storage spool, the second gear being engaged with the first gear.

19. A tissue puncture closure device according to claim 12 further comprising an anchor, the sealing plug being arranged adjacent to and proximal of the anchor.

20. A tissue puncture closure device according to claim 19 wherein the tamping member compacts the sealing plug against the anchor.

\* \* \* \* \*